United States Patent
Ormsby et al.

(10) Patent No.: US 9,326,819 B2
(45) Date of Patent: May 3, 2016

(54) ELECTRICALLY TUNABLE TISSUE ABLATION SYSTEM AND METHOD

(75) Inventors: Theodore C. Ormsby, Escondido, CA (US); Russell Chung, San Diego, CA (US); George Leung, San Diego, CA (US); Gwo Jenn Shen, Carlsbad, CA (US)

(73) Assignee: Medwaves, Inc., San Diego, CA (US)

( * ) Notice: Subject to any disclaimer, the term of this patent is extended or adjusted under 35 U.S.C. 154(b) by 1127 days.

(21) Appl. No.: 12/424,274

(22) Filed: Apr. 15, 2009

(65) Prior Publication Data

US 2010/0268218 A1 Oct. 21, 2010

(51) Int. Cl.
*A61B 18/18* (2006.01)

(52) U.S. Cl.
CPC ............. *A61B 18/18* (2013.01); *A61B 18/1815* (2013.01); *A61B 2018/1869* (2013.01)

(58) Field of Classification Search
CPC ..................... A61B 18/18; A61B 2018/00875; A61B 2018/00577; A61B 2018/1869
USPC ................. 606/32, 33, 34, 41, 42, 48, 49, 50; 607/101, 102, 154, 156
See application file for complete search history.

(56) References Cited

U.S. PATENT DOCUMENTS

| | | | |
|---|---|---|---|
| 4,475,108 A | 10/1984 | Moser | |
| 5,164,688 A * | 11/1992 | Larson | ............................. 333/33 |
| 5,167,658 A * | 12/1992 | Ensslin | ............................. 606/34 |
| 5,405,346 A | 4/1995 | Grundy et al. | |
| 5,693,082 A | 12/1997 | Warner et al. | |
| 5,902,251 A | 5/1999 | vanHooydonk | |
| 5,904,709 A | 5/1999 | Arndt et al. | |
| 5,957,969 A | 9/1999 | Warner et al. | |
| 6,067,475 A | 5/2000 | Graves et al. | |
| 6,190,382 B1 | 2/2001 | Ormsby et al. | |
| 6,485,486 B1 | 11/2002 | Trembly et al. | |
| 6,648,883 B2 | 11/2003 | Francischelli et al. | |
| 6,663,625 B1 | 12/2003 | Ormsby | |
| 6,911,027 B1 * | 6/2005 | Edwards et al. | ................. 606/40 |
| 7,004,938 B2 | 2/2006 | Ormsby | |
| 7,070,595 B2 | 7/2006 | Ormsby et al. | |
| 7,367,972 B2 | 5/2008 | Francischelli et al. | |
| 2003/0078573 A1 | 4/2003 | Truckai et al. | |
| 2005/0184922 A1 | 8/2005 | Ida et al. | |
| 2005/0237131 A1 * | 10/2005 | Chang et al. | ................... 333/175 |
| 2006/0025758 A1 * | 2/2006 | Strul et al. | ........................ 606/32 |
| 2006/0287649 A1 * | 12/2006 | Ormsby | ............. A61B 18/1492 606/33 |
| 2006/0293649 A1 * | 12/2006 | Lorang et al. | .................... 606/32 |
| 2008/0015570 A1 | 1/2008 | Ormsby et al. | |
| 2009/0076492 A1 | 3/2009 | Behnke | |
| 2009/0082762 A1 | 3/2009 | Ormsby et al. | |

OTHER PUBLICATIONS

Notification, International Search Report and Written Opinion dated Nov. 30, 2010 for PCT/US10/31259.

* cited by examiner

*Primary Examiner* — Emily Schmidt
*Assistant Examiner* — Lauren M Peng
(74) *Attorney, Agent, or Firm* — Cesari and McKenna LLP

(57) ABSTRACT

An ablation system which transmits radio frequency (RF) energy for the ablation of biological tissues has a transmission line and an RF antenna disposed at the distal portion of the transmission line. An RF signal generator supplies RF energy to the proximal end of the cable for transmission to the antenna, and an electrically tunable transformer is connected between the signal generator and the antenna. The transformer is tuned based on detection of the reflected power level from the antenna so as to reduce or minimize reflected power, thereby increasing RF energy coupling between the antenna and tissue.

9 Claims, 3 Drawing Sheets

ELECTRICALLY TUNABLE TISSUE ABLATION SYSTEM AND METHOD

BACKGROUND

1. Field of the Invention

The present invention concerns a Radio Frequency (RF) based ablation system for ablating tissue and occlusions, particularly within liquid-filled lumens of animals, such as the heart, liver, arteries and vessels of a human, with an electrical field produced about an RF antenna, and is particularly concerned with a control system and method for electrically tuning the system to adapt the impedance of the RF power delivery to provide at least some compensation for variations in tissue load.

2. Related Art

Therapeutic tissue ablation systems apply energy to a biological ablation tissue site via different energy exchange means, such as heat conduction and irradiation. These systems may employ various energy modes, such as radiofrequency, ultrasound, laser, cryogenic, and the like. Within the radio frequency (RF) range, certain microwave ablation systems are used to destroy or ablate biological tissues. In one application, a microwave ablation system is used to ablate cardiac tissues that cause irregular heartbeats or arrhythmia, avoiding the need for more risky and invasive open heart surgery. In such an application, an ablation member such as an RF antenna is incorporated as part of a catheter. The catheter is passed through the vein for access to the atrium. Within the atrium, the RF antenna is positioned at the desired location where ablation is applied.

Microwave ablation systems can also be used in treatment of other biological sites such as arteries, organs and body vessels. As an example, a microwave ablation system is used to ablate tumors in the lungs, liver, kidney or other areas of the body.

These surgical and therapeutic applications require an efficient system for the transmission of radio frequency energy to the ablating member for the delivery of energy to the target tissue site. U.S. Patent Application Publication No. 20080015570 of Ormsby et al. describes a tissue ablation system comprising a hollow conductive coaxial cable having a first inner elongated electrically conductive tubular member having a distal end portion, the first tubular member having a hollow, axially extending lumen, a second elongated electrically conductive member disposed in a substantially coaxial relationship over at least a portion of the first electrically conductive tubular member over substantially the length of the cable, a dielectric medium disposed between the first and second electrically conductive tubular members, and an ablating member or radio-frequency antenna which delivers radio frequency energy including microwaves to body tissue disposed at the distal end portion of the cable. The radiofrequency antenna is adapted to receive and irradiate radiofrequency energy in the microwave range at a frequency typically greater than 300 Megahertz (MHz) in the electromagnetic spectrum for ablating biological tissue along a biological ablation pathway.

Typical microwave tissue ablation systems have a RF power supply which provides RF energy along the coaxial cable or waveguide to the antenna. Most current tissue ablation systems are designed to provide a set impedance, which may be of the order of 50 ohms. However, the impedance on the catheter side of the system tends to vary, for example due to coaxial cable characteristics and variations in the electromagnetic properties of the tissue under treatment. It is known that the dielectric constants of different types of tissue, for example heart tissue and liver tissue, are different. Also, the dielectric properties of the tissue change as the tissue is treated. This prevents a fixed electromagnetic RF supply circuit from achieving maximum performance in delivering the highest amount of RF energy to the tissue being treated. In U.S. Pat. No. 6,190,382 of Ormsby, a microstrip transformer between the RF energy source and the transmission line or catheter is used to adapt the 50 ohm system more closely to the ablation antenna impedance.

In U.S. Pat. No. 7,070,595 of Ormsby et al., a tissue ablation system and method is described in which the output frequency of the RF energy pulses supplied to the catheter is adjusted to effect a substantial match with the RF antenna and biological tissue load impedance. In this system, a bi-directional coupler samples the forward pulses supplied to the microwave transmission line or co-axial cable and the reflected pulses which are reflected from the target ablation tissue, and uses the signal samples as feedback to a controller which varies the frequency in order to reduce the reflected signal, so that more energy is applied to the tissue undergoing ablation. U.S. Pat. No. 5,957,969 of Warner et al. describes a mechanically tuned microwave ablation catheter system and method which has a tuner located in the power supply, the transmission line, or the antenna which changes the antenna configuration, moves material relative to the antenna, or alters the waveguide.

SUMMARY

The present invention provides an improved radio frequency based ablation system is provided for ablating biological tissues of a body vessel, including the atrium of a patient.

In one embodiment, a radio frequency (RF) based tissue ablation system comprises a RF generator in the microwave frequency range adapted for communicating RF energy to a waveguide or probe that is adaptable for positioning at a biological treatment site or insertion in a body vessel. The waveguide comprises an RF transmission line and an RF antenna provided at the distal portion of the waveguide to receive and transmit radio frequency energy for tissue ablation. After the RF antenna is positioned within the body vessel, the RF generator is activated to apply energy to the antenna. In one embodiment, an electronically tunable transformer is connected between the RF generator and the RF transmission line and the transformer is tuned in response to detection of a reflected signal from the transmission line which is above a predetermined value, so as to reduce return losses.

Reflected signals in ablation systems are due to mismatch between the impedance of the power supply or RF signal generator and the impedance of the transmission line and antenna. The impedance of the antenna varies according to the electromagnetic properties of the tissue to which the antenna output is directed. The electronically tunable transformer may be located in a handle at the proximal end of the transmission line, and adapts the impedance of the RF signal generator to the impedance of the ablation antenna. In one embodiment, a directional coupler is connected between the transformer and the antenna, and the reflected power is detected by a detection device connected to the directional coupler. The detection device has an output proportional to the detected reflected power level, and the output is connected to a controller which tunes the transformer so as to minimize or reduce the reflected power level detected by the detector. This adapts the antenna so that less energy is reflected and thus more energy is applied to the tissue.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Certain embodiments as disclosed herein provide for a radio frequency energy transmission device, which incorporates a transmission line for conducting radio frequency (RF) energy, particularly microwave energy, for the ablation of biological tissues. The transmission line may comprise coaxial inner and outer conductors which extend up to a distal portion of the cable. An ablating member such as a radio frequency (RF) antenna which delivers radio frequency energy, particularly microwave energy, is located at the distal portion of the cable. An RF generator is connected to the proximal end of the cable via an electronically tunable transformer and a control circuit associated with the transformer is adapted to reduce or minimize reflected power detected by a detector device at the transformer.

After reading this description, it will become apparent to one skilled in the art how to implement the invention in various alternative embodiments and alternative applications. However, although various embodiments of the present invention will be described herein, it is understood that these embodiments are presented by way of example only and not limitation. As such, this detailed description of various alternative embodiments should not be construed to limit the scope or breadth of the present invention as set forth in the appended claims.

Figure 1:
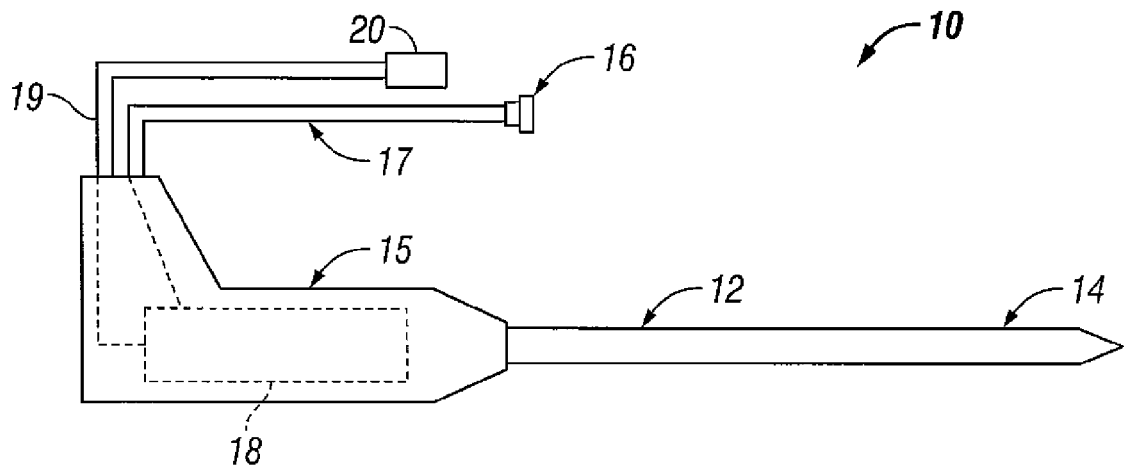
FIG. 1 is a schematic diagram of an ablation device incorporating a transformer and control circuit for adjusting the transformer properties.

FIG. 1 illustrates one embodiment of a radio frequency (RF) ablation system comprising a radio frequency signal generator or power supply (not illustrated) for generating an RF signal and a wave guide device or probe 10 which receives the RF signal. The device 10 comprises a wave guide or RF transmission line 12 and a radio frequency (RF) ablation antenna 14 at the distal end portion of the wave guide which is adapted for positioning adjacent a biological tissue site. The microwave ablation system is similar to that described in co-pending application Ser. No. 11/781,467 filed on Jul. 23, 2007 and Ser. No. 11/858,736 filed on Sep. 20, 2007, the contents of both of which are incorporated herein by reference, but includes a tuning control circuit 18 which is designed to modify the effective impedance at the RF generator end of the system based on a detected reflected power from the wave guide device or probe. The wave guide may comprise inner and outer electrically conductive members or coaxial conductors which extend coaxially from a handle 15 at the proximal end of the apparatus and which provide the transmission line for transmitting an RF signal to the antenna.

The RF or microwave signal generator is connected to the wave guide via a connector 16 and a coaxial cable 17 which is connected to the control circuit 18 mounted in the handle 15. Output signals from the waveguide are connected through the handle and via signal cable 19 and signal connector 20 to a signal processor (not illustrated), for example as described in co-pending application Ser. No. 11/479,259 filed on Jun. 30, 2006, the contents of which are incorporated herein by reference. A temperature detection circuit may also be located on a PCB within the handle to connect a temperature sensor signal received from a temperature sensor within the probe 10 to signal cable 19.

One problem with prior art tissue ablation systems is that the effective impedance of the wave guide and antenna is often not well matched to the effective impedance of the tissue being treated. The dielectric constant and the conductance of various human tissues vary. For example, according to the database compiled by Federal Communications Commission (FCC) (www.fcc.gov/fcc-bin/dielec.sh), the dielectric constant and conductance of the liver is 46.76 and 0.86 Siemens respectively while the muscle exhibits a dielectric constant of about 56.5 and conductance of 1.00 Siemens. Furthermore, during the ablation process, the dynamic interaction between the tissue and the microwave energy continuously modifies the actual electromagnetic properties of the tissue. This limits the ability of a fixed electromagnetic circuit to achieve its maximum performance in delivering the highest amount of RF power to the tissue being treated.

Although the impedance reference used in most microwave systems is commonly set at 50 Ohm, this is not a convenient value due to the excessive size of the cable diameters being used in the ablation process. A smaller cable diameter is desirable in limiting the incision at the entry point of the tissue, and this means that the standard 50 Ohm impedance level is not ideal. Further complication arises as the final impedance of the ablation antenna is a combination of the cable characteristics and the electromagnetic properties of the tissue. The concept of using a printed circuit board (PCB) transformer to adapt the 50 Ohm system more closely to the ablation antenna impedance is described, for example, in U.S. Pat. No. 6,190,382 of Ormsby, the contents of which are incorporated herein by reference. However, this still provides one fixed impedance value (typically around 30 Ohms) which is not ideal in all situations.

Figure 2:
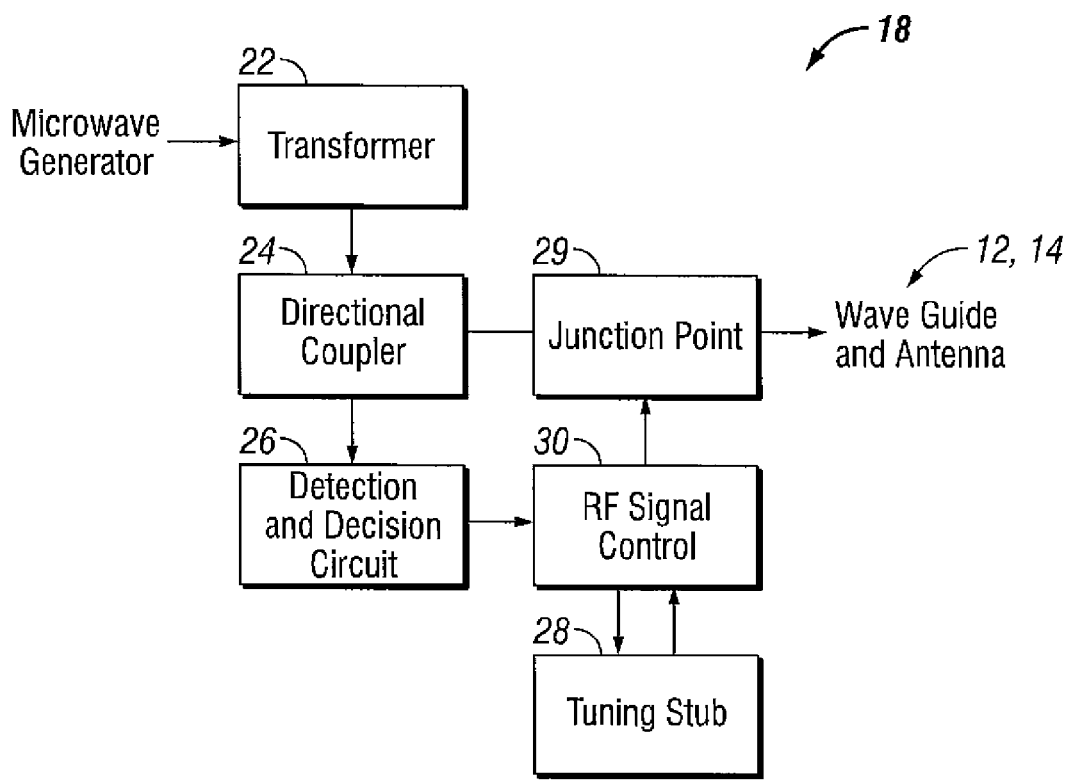
FIG. 2 is a schematic block diagram, partly broken away, of one embodiment of a transformer control circuit for adapting the impedance of the transformer based on a detected reflected signal.
Figure 3:
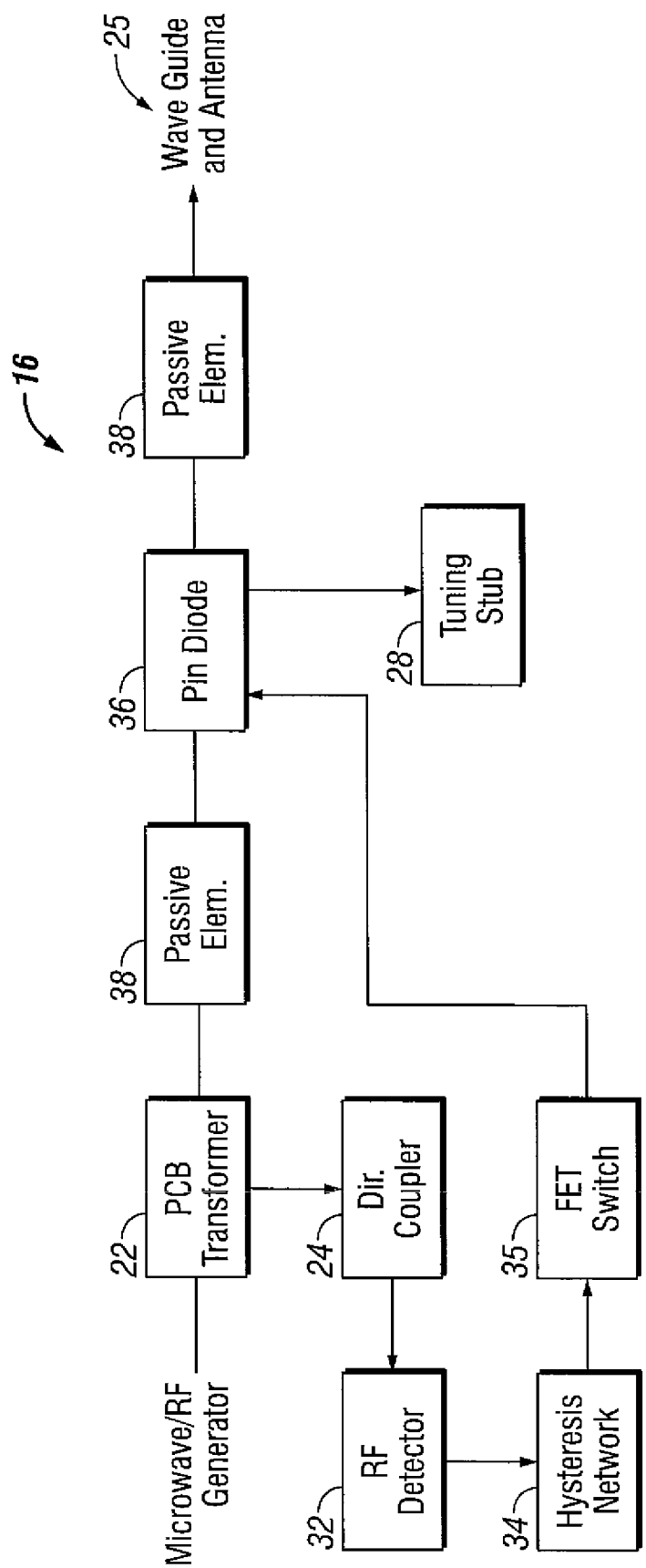
FIG. 3 is a more detailed block diagram of the circuit of FIG. 2.
Figure 5:
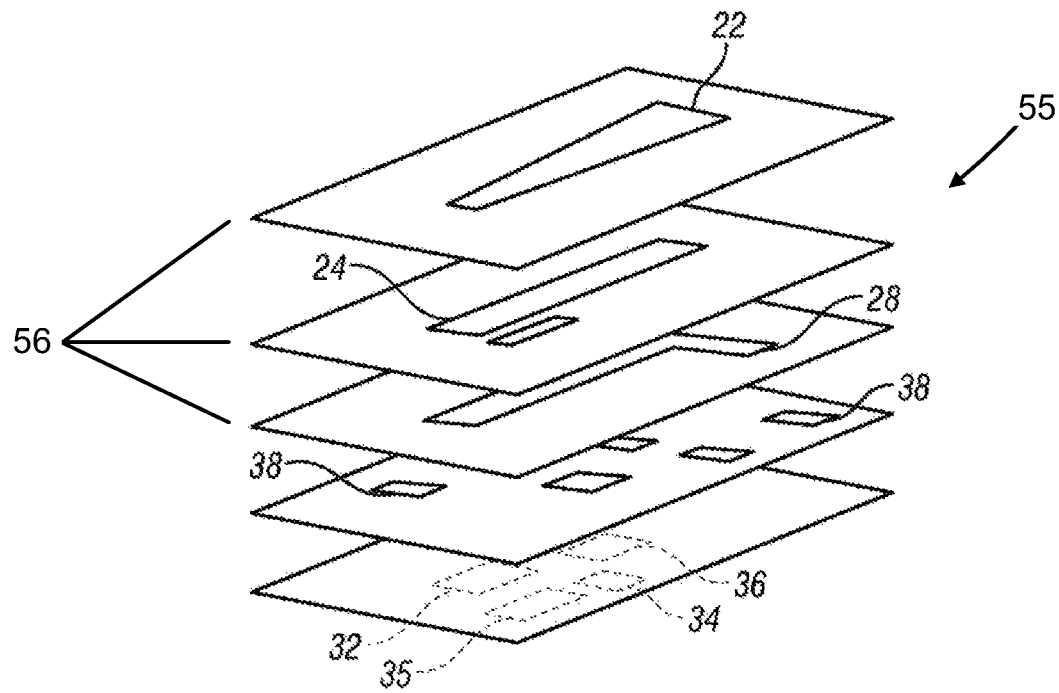
FIG. 5 illustrates one embodiment of a multi-layer arrangement of the components of the control circuit of FIG. 3.

FIGS. 2 and 3 illustrate one embodiment of a control circuit or system 18 which includes a transformer 22 and a tuning section which adapts the effective impedance of the transformer based on a detected reflected signal. In the illustrated embodiment, the circuit 16 is sufficiently compact to allow it to be mounted in the handle 12 of a microwave antenna probe or cable device 10, as illustrated in FIG. 1. In one embodiment, the circuit may be provided on a printed circuit board, or may be fabricated on a compact, multi-layer substrate using low temperature, co-fire ceramic (LTCC) technology, as illustrated in FIG. 5, for example. Mounting of the impedance modification system in the handle of the ablation probe or cable device places it relatively close to the ablation antenna, reducing losses.

As noted above, some ablation systems utilize a PCB transformer to efficiently transfer the microwave energy to the tissue being treated. However, these systems produce a constant impedance step down and are not adaptable for use with different tissues which exhibit different dielectric constants or which have properties which vary over time, for example as a result of tissue ablation. When the transformer is properly designed so that the impedance of the microwave power supply closely matches the effective impedance of the antenna and surrounding tissue, the return loss or reflected signal, as seen by the control circuit, is minimal. However, as the tissue load changes, the return loss increases. The control or tuning system and method of FIGS. 2 to 4 modifies the transformer to vary the effective impedance of the microwave power supply depending on the detected reflected signal, which in turn is dependent on the effective impedance of the tissue being treated. By modifying the transformer characteristics, such return losses can be decreased.

As illustrated in FIG. 2, the control or impedance tuning circuit basically comprises transformer 22 which is connected to the microwave signal cable from the microwave power supply or generator, and a directional coupler 24 connected between the transformer 22 and the input to wave guide or transmission line 12. A detection and decision circuit 26 is also connected to directional coupler 24 to monitor reflected signal from the wave guide 25. A tuning stub 28 is connected into the signal line between the microwave generator and antenna at junction point 29 when the reflected signal exceeds a predetermined value, as described below in connection with FIG. 3, via RF signal controller or switch 30 which is controlled by the detection and decision circuit 26. This effectively modifies or adds to the length of the transformer and changes the effective impedance of the microwave power supply so that less power is reflected.

FIG. 3 is a more detailed block diagram illustrating the components of one embodiment of the control circuit of FIG. 2. In this embodiment, the transformer may be implemented as a microstrip transformer 22. The amount of RF energy being reflected by the unmatched load is sampled by the directional coupler 24 and detected by an RF detector 32, which may be a detector diode. RF detector 32 has an output which is connected to a hysteresis network 34 which provides hysteresis for the control circuit. Such a network could be implemented by many schemes, including the Schmitt trigger method. The output of hysteresis network 34 is connected to an FET switch 35. The output of FET switch 35 is connected to a RF PIN diode 36, which is also connected to tuning stub 28. Passive elements 38 such as inductive or capacitive elements are provided on each side of PIN diode 36 for termination of the tuning section.

The reflected power from the probe is detected or sampled by the directional coupler, and is converted to a DC voltage by means of the RF detection diode 32. As the electromagnetic properties of the tissue change during the ablation procedure, the reflected power increases, and when the resultant increase in voltage is sufficient to operate the FET switch 35, the FET is switched on, in turn switching on the PIN diode 36 to connect the tuning stub or tuning stub section 28 into the circuit, thus reducing the reflected power and increasing energy delivery to the tissue surrounding the probe antenna.

Figure 4:
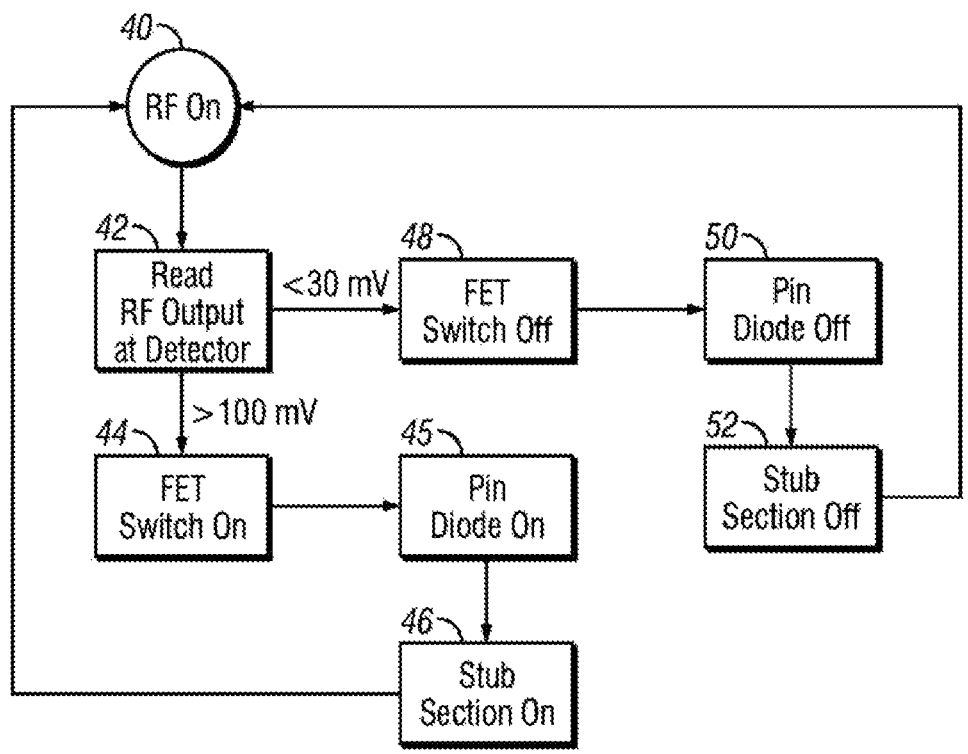
FIG. 4 is a flow diagram illustrating one embodiment of a method for controlling the impedance of the transformer in the circuit of FIGS. 2 and 3.

FIG. 4 illustrates one embodiment of a method for varying the effective impedance of the microwave power supply between two values based on detected reflected power. As soon as the radio frequency or microwave generator is switched on (step 40), the reflected RF output at directional coupler 24 is converted to a voltage and read at detector 32 (step 42). If the voltage is higher than a predetermined maximum value, which is 100 mV in this embodiment but may be a different selected value in alternative embodiments, the FET 35 is switched on (step 44), which in turn switches on the PIN diode 36 (step 45) and the tuning stub or stub section 28 (step 46), effectively increasing the impedance of the RF power supply side of the system. The directional coupler continues to sample the reflected power, and the reflected power is converted to a DC voltage at detector 32. As long as the detected voltage is above a predetermined value, the stub section remains on. If it falls below a selected minimum value, the FET 35 is switched off (step 48), which in turn switches off the PIN diode 36 (step 50) and the tuning stub 28 (step 52). In one embodiment, the minimum reflected power signal value at which the tuning stub is disconnected is 30 mV, while the maximum reflected power signal value before the tuning stub is connected into the circuit is 100 mV, as indicated in FIG. 4, but other maximum and minimum values for controlling switching of the tuning section into and out of the circuit may be selected in alternative embodiments. The hysteresis device or network 34 makes the circuit less susceptible to noise and reduces the risk of switching too quickly between the two impedance levels.

Since the control circuit is provided in the handle 15, it should be made relatively small due to the space constraints. In one embodiment, the control circuit 18 is implemented in a single layer on a printed circuit board. Since conventional circuit board manufacturing technology does not permit passive elements being embedded in the substrate, only the microstrip transformer and the tuning section are included in the PCB substrate. The rest of the components are applied separately to a surface of the PCB substrate.

In other embodiments, the control circuit or system may be fabricated using low temperature co-fire ceramic (LTCC) or thick film hybrid technology. LTCC technology allows many RF passive components be integrated in a compact manner. FIG. 5 illustrates one embodiment of the control circuit or system integrated into a multi-layer LTCC device 55. One advantage of LTCC technology is that it allows many layers to be stacked together, combined with via-contacts between these layers. As illustrated in FIG. 5, the control device 55 has multiple LTCC layers 56 with components integrated into the layers or provided on selected sides of the layers and connected to components in adjacent layers by via contacts. In FIG. 5, the components mounted on the bottom side of the lowermost layer are indicated in dotted outline.

The tuning system and method in the embodiments described above allows the effective impedance at the power supply side of a microwave ablation system to be varied between two different values depending on detected reflected power. As long as the detected reflected power level is below a predetermined maximum value, the impedance remains at an initial, lower setting. However, if the detected power level exceeds the predetermined maximum value, a tuner stub section is connected into the circuit and the impedance is increased to a second, higher value. The tuner stub section remains on as long as the detected reflected power is above a predetermined minimum value. If the detected reflected power falls below the minimum value, the tuner stub section is switched off. The effectiveness of the tuning system is increased due to its location in the handle of the probe or ablation device, close to the antenna which transmits RF or microwave energy to the surrounding tissue. The tuning system is designed to be relatively compact so as to fit into the relatively small space available in the handle. This system allows the transformer to be modified based on the dielectric properties of the tissue to be treated, rather than having to select a completely different ablation device for different types of tissue. The system may provide for more than two different impedance values by incorporating additional tuning stubs which can be selectively switched on at different reflected power levels.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are, therefore, representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

The invention claimed is:

1. A microwave ablation system, comprising:
a radio frequency (RF) antenna for positioning adjacent a biological tissue site;
a transmission line having a first end connected to the RF antenna and a second end;
an RF signal generator adapted to generate a train of RF pulses in the transmission line for transmission to the RF antenna;
an impedance control circuit between the first end of the transmission line and the RF signal generator which is configured to modify the impedance of the RF signal generator part of the system based on a detected reflected power signal when the antenna is positioned adjacent the biological tissue site to be treated, the impedance control circuit comprising a printed circuit board;
the impedance control circuit comprising a transformer which modifies the effective impedance of the power supply, a tuning stub which is selectively connected with the transformer in order to adjust the effective impedance of the impedance control circuit between two different impedances, a detector which monitors the reflected signal and a controller which receives the detector output and which is configured to control connection of the tuning stub to the transformer and disconnection of the tuning stub from the transformer based on the detected reflected power signal level, whereby the impedance control circuit has a first impedance when the tuning stub is not connected to the transformer and a second impedance higher than the first impedance when the tuning stub is connected to the transformer, the controller being configured to connect the tuning stub to the transformer when the reflected power signal is above a first predetermined value and to disconnect the tuning stub from the transformer when the reflected power signal is below a second predetermined value; and
the impedance control circuit comprises a plurality of components and multiple layers of a monolithic substrate material, each layer carrying selected components of the impedance control circuit, and the tuning stub alone being integrated into one layer of the monolithic substrate material stacked between adjacent layers.

2. A microwave ablation system, comprising:
a radio frequency (RF) antenna for positioning adjacent a biological tissue site;
a transmission line having a first end connected to the RF antenna and a second end;
an RF signal generator adapted to generate a train of RF pulses in the transmission line for transmission to the RF antenna;
an impedance control circuit between the first end of the transmission line and the RF signal generator which is configured to switch the impedance of the RF signal generator part of the system solely between first and second different discrete impedances based on a detected reflected power signal when the antenna is positioned adjacent the biological tissue site to be treated, the second impedance being higher than the first impedance; and
the impedance control circuit comprising a transformer which modifies the effective impedance of the power supply, a tuning stub which is selectively connected with the transformer in order to adjust the effective impedance of the impedance control circuit between the first and second discrete impedances, a detector which monitors the reflected signal and a controller which receives the detector output and which is configured to control connection of the tuning stub to the transformer and disconnection of the tuning stub from the transformer based on the detected reflected power signal level, whereby the impedance control circuit has the first impedance when the tuning stub is not connected to the transformer and the second impedance when the tuning stub is connected to the transformer, the controller being configured to connect the tuning stub to the transformer when the reflected power signal is above a first predetermined value and to disconnect the tuning stub from the transformer when the reflected power signal is below a second predetermined value.

3. The system of claim 2, further comprising a handle at the second end of the transmission line, the impedance control circuit being mounted in the handle.

4. The system of claim 3, wherein the impedance control circuit comprises a printed circuit board.

5. The system of claim 3, wherein the impedance control circuit is implemented on a multiple layer, low temperature co-fire ceramic (LTCC) substrate.

6. The system of claim 2, wherein the first predetermined value is 100 mV.

7. The system of claim 2, wherein the second predetermined value is 30 mV.

8. The system of claim 2, wherein the controller comprises a switch which switches on the tuning stub when the reflected signal is above the first predetermined value and which switches off the tuning stub when the reflected signal is below the first predetermined value.

9. The system of claim 8, wherein the impedance control circuit further comprises a hysteresis device between the detector and the switch configured to delay switching between the two impedance values.

* * * * *